United States Patent
Chew

(10) Patent No.: US 10,952,480 B1
(45) Date of Patent: Mar. 23, 2021

(54) FLUID-ABSORBING SCROTUM SHIELD AND ASSOCIATED USE THEREOF

(71) Applicant: Paxton Chew, Los Angeles, CA (US)

(72) Inventor: Paxton Chew, Los Angeles, CA (US)

(*) Notice: Subject to any disclaimer, the term of this patent is extended or adjusted under 35 U.S.C. 154(b) by 420 days.

(21) Appl. No.: 15/797,289

(22) Filed: Oct. 30, 2017

Related U.S. Application Data

(60) Provisional application No. 62/414,004, filed on Oct. 28, 2016.

(51) Int. Cl.
*A61F 6/04* (2006.01)
*A41D 27/12* (2006.01)

(52) U.S. Cl.
CPC .......... *A41D 27/12* (2013.01); *A41D 2400/60* (2013.01)

(58) Field of Classification Search
CPC .... A41D 27/12; A41D 13/0525; A41D 1/088; A61F 2006/041; A61F 2006/044; A61F 2006/045; A61F 5/451; A61F 5/453; A61F 5/455; A61F 6/04; A61F 5/445; A61F 5/448; A61F 2005/4483; A61F 2005/4486; A61M 25/0017; A41B 9/02; A41B 9/023; A41B 9/026
USPC ................................................. 128/889, 891
See application file for complete search history.

(56) References Cited

U.S. PATENT DOCUMENTS

| | | | | |
|---|---|---|---|---|
| 850,298 | A * | 4/1907 | De Mars | A41B 9/023 2/403 |
| 1,477,187 | A * | 12/1923 | Rayne | A61F 5/40 602/71 |
| 2,294,066 | A * | 8/1942 | Baehler | A61F 5/40 602/70 |
| 3,518,995 | A * | 7/1970 | Claff | A61F 6/02 128/842 |
| 3,621,846 | A * | 11/1971 | Lehman | A61F 5/40 602/67 |
| 4,387,726 | A * | 6/1983 | Denard | A61F 5/453 600/573 |
| 4,622,962 | A * | 11/1986 | Kauffman | A61F 5/40 602/70 |
| 4,771,477 | A * | 9/1988 | Cahill | A42B 1/208 2/12 |
| 6,862,746 | B2 * | 3/2005 | Cym | A41B 9/023 2/403 |
| 7,434,273 | B2 * | 10/2008 | Chung | A41B 9/023 2/403 |

* cited by examiner

*Primary Examiner* — Ophelia A Hawthorne
*Assistant Examiner* — Camtu T Nguyen
(74) *Attorney, Agent, or Firm* — Ashkan Najafi

(57) ABSTRACT

A fluid-absorbing scrotum shield includes a single and unitary body having a penis-receiving flange and a scrotum-containing pouch statically attached to the penis-receiving flange. The scrotum-containing pouch is suitably sized and shaped to receive an existing male scrotum such that the scrotum-containing pouch is intercalated between the existing male scrotum and an existing male penis extended through the penis-receiving flange and downward past the existing male scrotum. Each of the penis-receiving flange and the scrotum-containing pouch include fluid-absorbent material impregnated throughout an entire surface area thereof, respectively, to absorb sweat and other body fluids.

6 Claims, 3 Drawing Sheets

FLUID-ABSORBING SCROTUM SHIELD AND ASSOCIATED USE THEREOF

CROSS REFERENCE TO RELATED APPLICATIONS

This is a non-provisional patent application that claims the benefit of U.S. provisional patent application No. 62/414,004 filed Oct. 28, 2016, which is incorporated by reference herein in its entirety.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND

Technical Field

Exemplary embodiment(s) of the present disclosure relate to hygiene products and, more particularly, to a fluid-absorbing scrotum shield including an interior scrotum-containing pouch that serves as a protective housing for the scrotum thereby holding testicles and wicking away moisture from sweat, while reducing skin to skin contact, thus preventing discomfort and chafing in this genital area.

Prior Art

Typically, as men age, their testicles tend to hang lower with each passing year; as a result, these men are more susceptible to excessive sweat and moisture accumulation in the scrotum area, leading to discomfiting itching and chafing around the testicles and upper thighs.

Accordingly, a need remains for a fluid-absorbing scrotum shield in order to overcome at least one aforementioned shortcoming. The exemplary embodiment(s) satisfy such a need by providing a fluid-absorbing scrotum shield including an interior scrotum-containing pouch that serves as a protective housing for the scrotum that is convenient and easy to use, lightweight yet durable in design, versatile in its applications, and designed for holding testicles and wicking away moisture from sweat, while reducing skin to skin contact, thus preventing discomfort and chafing in this genital area.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a fluid-absorbing scrotum shield for holding male user testicles and wicking away sweat moisture therefrom, while reducing skin to skin contact, thus preventing discomfort and chafing in a male genital area. These and other objects, features, and advantages of the non-limiting exemplary embodiment(s) are provided by a fluid-absorbing scrotum shield including a single and unitary body having a penis-receiving flange and a scrotum-containing pouch statically attached to the penis-receiving flange. Advantageously, scrotum-containing pouch is suitably sized and shaped to receive an existing male scrotum such that the scrotum-containing pouch is intercalated between the existing male scrotum and an existing male penis extended through the penis-receiving flange and downward past the existing male scrotum. Notably, each of the penis-receiving flange and the scrotum-containing pouch include fluid-absorbent material impregnated throughout an entire surface area thereof, respectively, to absorb sweat and other body fluids.

In a non-limiting exemplary embodiment, the penis-receiving flange is located at a top end of the body. In this manner, the scrotum-containing pouch is integrally connected to the penis-receiving flange and extended downwardly to a bottom end of the body.

In a non-limiting exemplary embodiment, the penis-receiving flange includes an outer curvilinear surface continuously projected upwardly from the scrotum-containing pouch, an aperture spaced interior of the outer curvilinear surface, and a plurality of slits disposed along an inner circumferential edge of the aperture as well as a portion of a posterior face of the flange. Advantageously, a diameter of the aperture is resiliently morphed, by expansion and contraction of the slits, when the existing male penis is penetrated through the aperture. Thus, the existing male penis is maintained at a substantially stable position during walk, sitting, and other moving conditions.

In a non-limiting exemplary embodiment, the slits traverse a cross-sectional thickness of the inner circumferential edge of the aperture.

In a non-limiting exemplary embodiment, the slits are equidistantly spaced about a centrally registered axis passing through the aperture.

In a non-limiting exemplary embodiment, the slits terminate interior of the outer curvilinear surface.

In a non-limiting exemplary embodiment, the scrotum-containing pouch includes an open posterior side, a closed anterior side, and a cup-shaped cavity intermediately situated between the open posterior side and the closed anterior side. Such a cup-shaped cavity has a substantially smooth interior surface for providing a comfortable resting surface for the existing male scrotum.

In a non-limiting exemplary embodiment, the cup-shaped cavity is disposed subjacent to the penis-receiving flange such that the closed anterior side extends entirely from the bottom end of the body to the penis-receiving flange. Such a structural configuration provides a continuous and uninterrupted surface area against which both the existing male scrotum and existing male penis abut (thereby wicking sweat and other body fluids).

The present disclosure further includes a method of utilizing a fluid-absorbing scrotum shield for holding male user testicles and wicking away sweat/moisture therefrom, while reducing skin to skin contact, thus preventing discomfort and chafing in a male genital area. Such a method includes the initial step of: providing a single and unitary body including a penis-receiving flange and a scrotum-containing pouch statically attached to the penis-receiving flange, wherein each of the penis-receiving flange and the scrotum-containing pouch include fluid-absorbent material impregnated throughout an entire surface area thereof, respectively.

The method further includes the steps of: preventing direct skin to skin contact between the existing male penis and the existing male scrotum by performing the sub-steps of: extending the existing male penis through the penis-receiving flange; the scrotum-containing pouch receiving an existing male scrotum; and positioning the existing male penis along a closed posterior side of the scrotum-containing pouch such that the scrotum-containing pouch is intercalated between the existing male scrotum and the existing male penis extended through the penis-receiving flange and downward past the existing male scrotum.

There has thus been outlined, rather broadly, the more important features of non-limiting exemplary embodiment (s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

Figure 1:
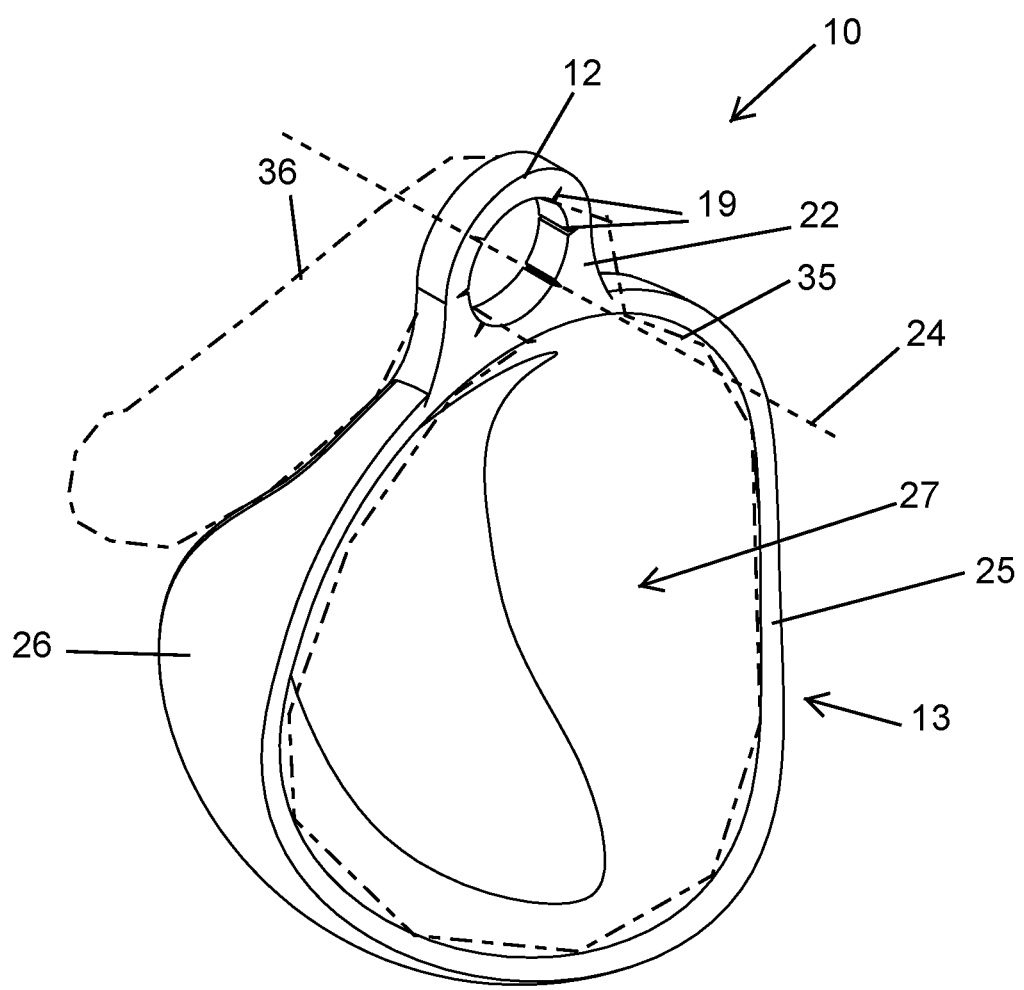
FIG. 1 is a perspective view of a fluid-absorbing scrotum shield, in accordance with a non-limiting exemplary embodiment.
Figure 2:
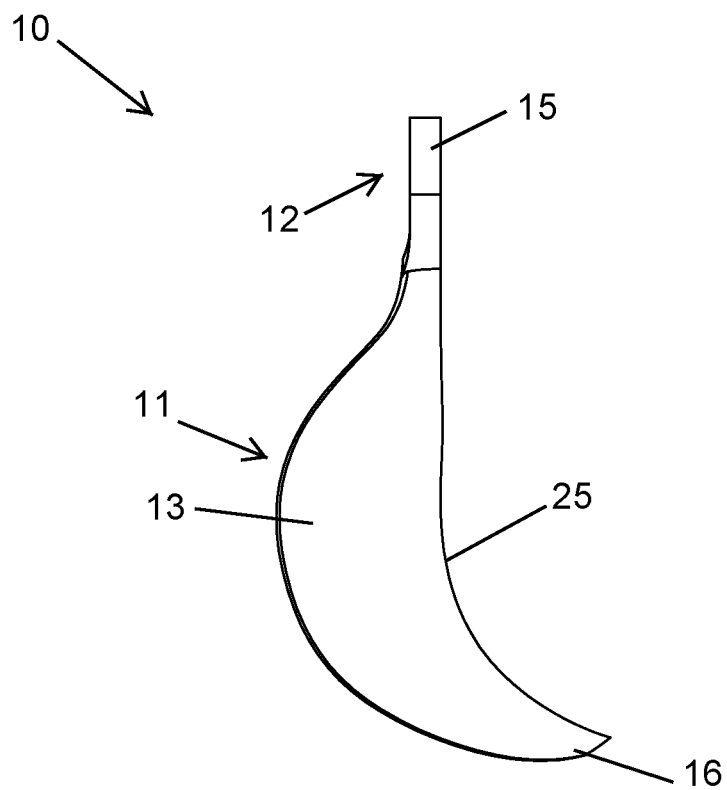
FIG. 2 is a side-elevational view of the fluid-absorbing scrotum shield shown in FIG. 1.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment (s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

If used herein, "about" means approximately or nearly and in the context of a numerical value or range set forth means±15% of the numerical.

If used herein, "substantially" means largely if not wholly that which is specified but so close that the difference is insignificant.

A non-limiting exemplary embodiment(s) of the present disclosure is referred to generally in FIGS. 1-4a and is intended to provide a fluid-absorbing scrotum shield 10 including an interior scrotum-containing pouch 13 that serves as a protective housing for the scrotum thereby holding testicles and wicking away moisture from sweat, while reducing skin to skin contact (between the existing male scrotum 35 and existing male penis 36), thus preventing discomfort and chafing in this genital area. It should be understood that the exemplary embodiment(s) may be used to shield large and small testicle(s), and should not be limited to any particular sized testicle(s) described herein.

The non-limiting exemplary embodiment(s) is referred to generally in FIGS. 1-4a and is intended to provide a fluid-absorbing scrotum shield 10 for holding male user testicles and wicking away sweat moisture therefrom, while reducing skin to skin contact (between the existing male scrotum 35 and existing male penis 36), thus preventing discomfort and chafing in a male genital area. Such a fluid-absorbing scrotum shield 10 includes a single and unitary body 11 having a penis-receiving flange 12 and a scrotum-containing pouch 13 statically attached to the penis-receiving flange 12. Advantageously, scrotum-containing pouch 13 is suitably sized and shaped to receive an existing male scrotum 35 such that the scrotum-containing pouch 13 is intercalated between the existing male scrotum 35 and an existing male penis 36 extended through the penis-receiving flange 12 and downward past the existing male scrotum 35. Notably, each of the penis-receiving flange 12 and the scrotum-containing pouch 13 include fluid-absorbent material 14 impregnated throughout an entire surface area thereof, respectively, to absorb sweat and other body fluids.

In a non-limiting exemplary embodiment, the penis-receiving flange 12 is located at a top end 15 of the body 11. In this manner, the scrotum-containing pouch 13 is integrally connected to the penis-receiving flange 12 and extended downwardly to a bottom end 16 of the body 11.

In a non-limiting exemplary embodiment, the penis-receiving flange 12 includes an outer curvilinear surface 17 continuously projected upwardly from the scrotum-containing pouch 13, an aperture 18 spaced interior of the outer curvilinear surface 17, and a plurality of slits 19 disposed along an inner circumferential edge 20 of the aperture 18 as well as a portion of a posterior face 22 of the flange 12. Advantageously, a diameter of the aperture 18 is resiliently morphed, by expansion and contraction of the slits 19, when the existing male penis 36 is penetrated through the aperture 18. Thus, the existing male penis 36 is maintained at a substantially stable position during walk, sitting, and other moving conditions.

In a non-limiting exemplary embodiment, the slits 19 traverse a cross-sectional thickness 23 of the inner circumferential edge 20 of the aperture 18.

In a non-limiting exemplary embodiment, the slits 19 are equidistantly spaced about a centrally registered axis 24 passing through the aperture 18.

Figure 3:
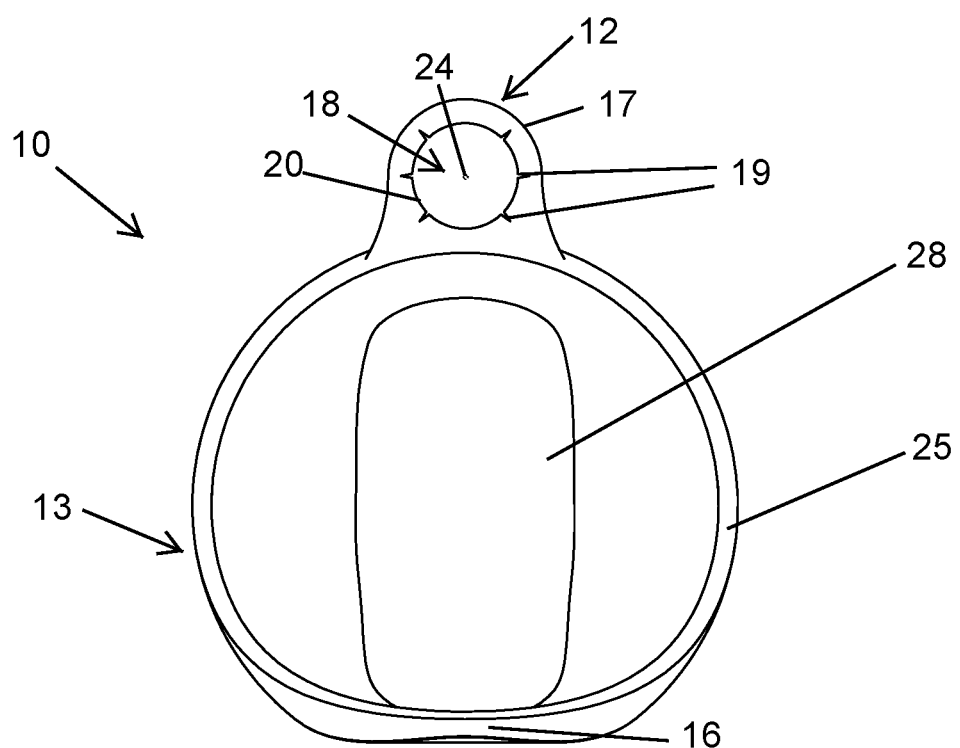
FIG. 3 is a front elevational view of the fluid-absorbing scrotum shield shown in FIG. 1.
Figure 4:
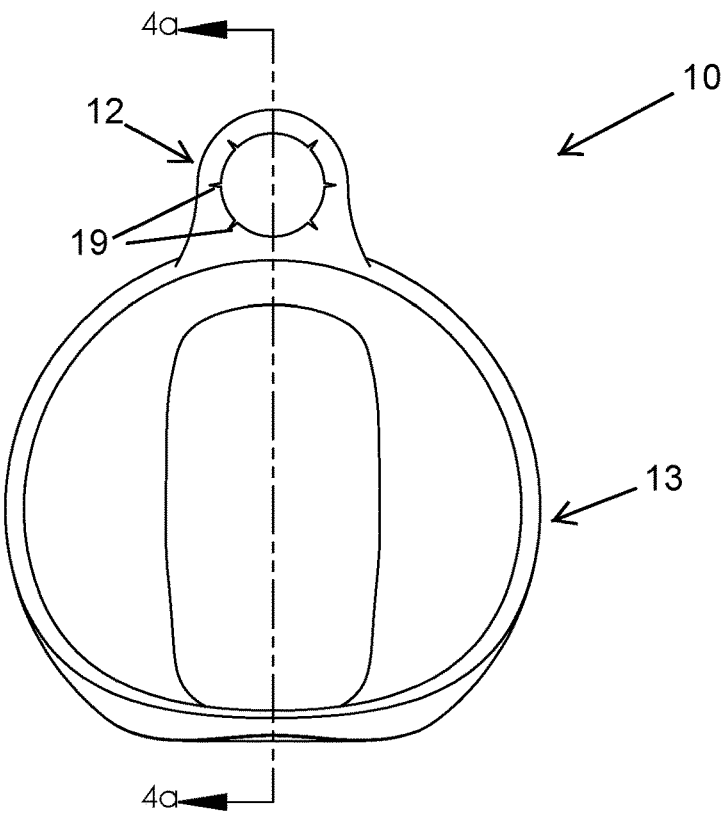
FIG. 4 is another front elevational view of the fluid-absorbing scrotum shield shown in FIG. 1, wherein cross-sectional line 4a-4a is illustrated.
Figure 4A:
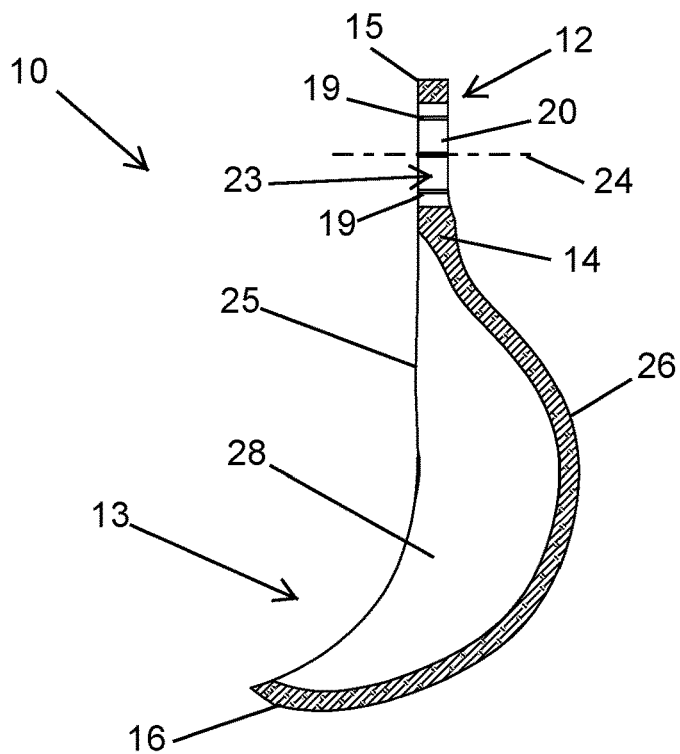
FIG. 4a is a cross-sectional view taken along line 4a-4a in FIG. 4.

In a non-limiting exemplary embodiment, as perhaps best shown in FIGS. 1 and 3-4, the slits 19 terminate interior of the outer curvilinear surface 17.

In a non-limiting exemplary embodiment, the scrotum-containing pouch 13 includes an open posterior side 25, a closed anterior side 26, and a cup-shaped cavity 27 intermediately situated between the open posterior side 25 and the closed anterior side 26. Such a cup-shaped cavity 27 has a substantially smooth interior surface 28 for providing a comfortable resting surface for the existing male scrotum 35.

In a non-limiting exemplary embodiment, the cup-shaped cavity 27 is disposed subjacent to the penis-receiving flange 12 such that the closed anterior side 26 extends entirely from the bottom end 16 of the body 11 to the penis-receiving flange 12. Such a structural configuration provides a continuous and uninterrupted surface area against which both the existing male scrotum 35 and existing male penis 36 abut (thereby wicking sweat and other body 11 fluids).

The present disclosure further includes a method of utilizing a fluid-absorbing scrotum shield 10 for holding male user testicles and wicking away sweat/moisture therefrom, while reducing skin to skin contact (between the existing male scrotum 35 and existing male penis 36), thus preventing discomfort and chafing in a male genital area. Such a method includes the initial step of: providing a single and unitary body 11 including a penis-receiving flange 12 and a scrotum-containing pouch 13 statically attached to the penis-receiving flange 12, wherein each of the penis-receiving flange 12 and the scrotum-containing pouch 13 include fluid-absorbent material 14 impregnated throughout an entire surface area thereof, respectively.

The method further includes the steps of: preventing direct skin to skin contact between the existing male penis 36 and the existing male scrotum 35 by performing the sub-steps of: extending the existing male penis 36 through the penis-receiving flange 12; the scrotum-containing pouch 13 receiving an existing male scrotum 35; and positioning the existing male penis 36 along a closed posterior side 25 of the scrotum-containing pouch 13 such that the scrotum-containing pouch 13 is intercalated between the existing male scrotum 35 and the existing male penis 36 extended through the penis-receiving flange 12 and downward past the existing male scrotum 35.

Referring to FIGS. 1-4a in general, in a non-limiting exemplary embodiment(s), fluid-absorbing scrotum shield 10 helps prevent skin to skin contact (between the existing male scrotum 35 and existing male penis 36), by serving as protective housing for the scrotum, thereby protecting this area from uncomfortable itching, chafing, rubbing, and sweating that can occur during the day as well as throughout the night. The fluid-absorbing scrotum shield 10 may be manufactured of a soft cotton or polycotton blend. Universal in design to accommodate the male genitalia, regardless of size, the product may measure approximately four inches (4") in length, three and one-half inches (3½") in width, and two and one-half inches (2½") in depth.

In a non-limiting exemplary embodiment, a top of the fluid-absorbing scrotum shield 10 boasts a small, expandable penis-receiving flange 12, provided to allow the wearer to comfortably insert the penis. Directly underneath is the testicle scrotum-containing pouch 13. This scrotum-containing pouch 13 is placed to cradle the scrotum, separating it from the shaft portion of the male penis 36 as it extends downward. In this manner, the accumulation of sweat in this area is blocked by the absorbent material 14 in the scrotum-containing pouch 13, alleviating moisture buildup that can invariably result in chafing and itching. This clever pouch 13 for the scrotum serves as a barrier against uncomfortable rubbing, another action that can cause irritation. By effectively separating the scrotum from the penis and thighs, the fluid-absorbing scrotum shield 10 may provide men of all ages, particularly older males, with non-cumbersome protection that can be worn whether at work or play, as well as overnight while sleeping.

Highly functional, the fluid-absorbing scrotum shield 10 is an innovative product that readily enhances male hygiene and overall health. Donned in a matter of seconds and conveniently disposable, this shield 10 offers extensive, yet discreet, protection for a delicate area of the anatomy. While the fluid-absorbing scrotum shield 10 is especially ideal for the older male population, men of all ages are sure to appreciate a product that is designed to specifically target a problem faced exclusively by men, and attends to a very important issue they face on a daily basis. Affordably priced, the fluid-absorbing scrotum shield 10 will be very well received by men from all walks of life, whether college students, professional executives, or retired seniors, an extremely sizable market potential.

While non-limiting exemplary embodiment(s) has/have been described with respect to certain specific embodiment (s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A fluid-absorbing scrotum shield for holding male user testicles and wicking away sweat moisture therefrom, while reducing skin to skin contact, thus preventing discomfort and chafing in a male genital area, said fluid-absorbing scrotum shield comprising:
    a body including a penis-receiving flange and a scrotum-containing pouch attached to said penis-receiving flange, said scrotum-containing pouch being adapted to receive an existing male scrotum such that said scrotum-containing pouch is capable of being intercalated between the existing male scrotum and an existing male penis extended through said penis-receiving flange and adapted to extend downward past the existing male scrotum;
    wherein each of said penis-receiving flange and said scrotum-containing pouch include fluid-absorbent material impregnated throughout an entire surface area thereof, respectively;
    wherein said penis-receiving flange is located at a top end of said body, wherein said scrotum-containing pouch is integrally connected to said penis-receiving flange and extended downwardly to a bottom end of said body;
    wherein said penis-receiving flange comprises:
    an outer curvilinear surface continuously projected upwardly from said scrotum-containing pouch;
    an aperture spaced interior of said outer curvilinear surface; and
    a plurality of slits disposed along an inner circumferential edge of said aperture as well as a portion of a posterior face of said penis-receiving flange;
    wherein a diameter of said aperture is resiliently morphed, by expansion and contraction of said plurality of slits, when the existing male penis is penetrated through said aperture;
    wherein said plurality of slits traverse a cross-sectional thickness of said inner circumferential edge of said aperture;
    wherein said plurality of slits are equidistantly spaced about a centrally registered axis passing through said aperture;
    wherein said plurality of slits terminate interior of said outer curvilinear surface.

2. The fluid-absorbing scrotum shield of claim 1, wherein said scrotum-containing pouch comprises:
    an open posterior side;
    a closed anterior side; and
    a cup-shaped cavity intermediately situated between said open posterior side and said closed anterior side, wherein said cup-shaped cavity has a substantially smooth interior surface.

3. The fluid-absorbing scrotum shield of claim 2, wherein said cup-shaped cavity is disposed subjacent to said penis-receiving flange such that said closed anterior side extends entirely from said bottom end of said body to said penis-receiving flange.

4. A fluid-absorbing scrotum shield for holding male user testicles and wicking away sweat moisture therefrom, while reducing skin to skin contact, thus preventing discomfort and chafing in a male genital area, said fluid-absorbing scrotum shield comprising:
    a single and unitary body including a penis-receiving flange and a scrotum-containing pouch statically attached to said penis-receiving flange, said scrotum-containing pouch being adapted to receive an existing male scrotum such that said scrotum-containing pouch is capable of being intercalated between the existing male scrotum and an existing male penis extended through said penis-receiving flange and adapted to extend downward past the existing male scrotum;
    wherein each of said penis-receiving flange and said scrotum-containing pouch include fluid-absorbent material impregnated throughout an entire surface area thereof, respectively;
    wherein said penis-receiving flange is located at a top end of said single and unitary body, wherein said scrotum-containing pouch is integrally connected to said penis-receiving flange and extended downwardly to a bottom end of said single and unitary body;
    wherein said penis-receiving flange comprises:
    an outer curvilinear surface continuously projected upwardly from said scrotum-containing pouch;
    an aperture spaced interior of said outer curvilinear surface; and
    a plurality of slits disposed along an inner circumferential edge of said aperture as well as a portion of a posterior face of said penis-receiving flange;
    wherein a diameter of said aperture is resiliently morphed, by expansion and contraction of said plurality of slits, when the existing male penis is penetrated through said aperture;
    wherein said plurality of slits traverse a cross-sectional thickness of said inner circumferential edge of said aperture;
    wherein said plurality of slits are equidistantly spaced about a centrally registered axis passing through said aperture;
    wherein said plurality slits terminate interior of said outer curvilinear surface.

5. The fluid-absorbing scrotum shield of claim 4, wherein said scrotum-containing pouch comprises:
    an open posterior side;

a closed anterior side; and a cup-shaped cavity intermediately situated between said open posterior side and said closed anterior side, wherein said cup-shaped cavity has a substantially smooth interior surface.

6. The fluid-absorbing scrotum shield of claim 5, wherein said cup-shaped cavity is disposed subjacent to said penis-receiving flange such that said closed anterior side extends entirely from said bottom end of said single and unitary body to said penis-receiving flange.

\* \* \* \* \*